United States Patent
Piasco et al.

(10) Patent No.: US 6,180,803 B1
(45) Date of Patent: Jan. 30, 2001

(54) 19-NOR-PREGNENE DERIVATIVES AND PHARMACEUTICALS CONTAINING SUCH DERIVATIVES

(75) Inventors: Alain Piasco; Jean Lafay; Rémi Delansorne; Jacques Paris; Jean-Claude Pascal, all of Nice (FR)

(73) Assignee: Laboratoire Theramex (MC)

( * ) Notice: Under 35 U.S.C. 154(b), the term of this patent shall be extended for 0 days.

(21) Appl. No.: 09/101,775

(22) PCT Filed: Jan. 17, 1997

(86) PCT No.: PCT/EP97/00357

§ 371 Date: Nov. 5, 1998

§ 102(e) Date: Nov. 5, 1998

(87) PCT Pub. No.: WO97/27210

PCT Pub. Date: Jul. 31, 1997

(30) Foreign Application Priority Data

Jan. 22, 1996 (EP) .................................................. 96400146

(51) Int. Cl.⁷ ............................. C07J 41/00; C07J 7/00; C07J 5/00

(52) U.S. Cl. ......................... 552/150; 552/515; 552/516; 552/519; 552/520; 552/557; 552/586; 552/592; 552/597; 552/511; 514/171; 514/177; 514/170

(58) Field of Search .................................... 552/516, 511, 552/519, 520, 557, 586, 592, 597; 514/178, 169, 170, 171, 177

(56) References Cited

U.S. PATENT DOCUMENTS 3,759,962 * 9/1973 Anner et al. ...................... 260/397.4
3,835,160 * 9/1974 Tanabe .............................. 260/340.9
3,891,677 * 6/1975 Tanabe .............................. 260/340.9

FOREIGN PATENT DOCUMENTS

1087127 * 8/1960 (DE).
1593524 * 8/1970 (DE).
2048231 * 4/1971 (DE).
 153270 * 8/1985 (EP).
1405214 * 9/1965 (FR).
1525916 * 10/1968 (FR).
2111097 * 6/1972 (FR).

OTHER PUBLICATIONS

R. Weichert (Experiencia, 23:10, (1967), pp. 794–796), 1967.*
Djerassi et al. (JACS, 78:11 (1956), pp. 2479–2481), 1967.*

* cited by examiner

Primary Examiner—Sabiha N. Qazi
(74) Attorney, Agent, or Firm—Dennison, Scheiner, Schultz & Wakeman

(57) ABSTRACT

The invention relates to compounds of the formula:

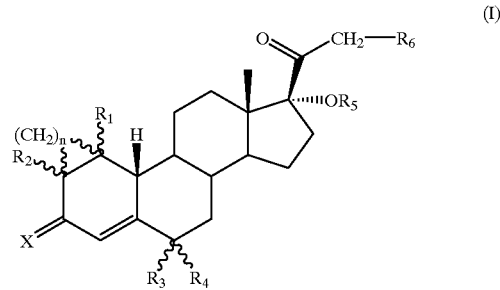

in which $R_1$, $R_2$, $R_3$, $R_4$, $R_5$, $R_6$, n and X are as defined in the specification, and to pharmaceutical compositions containing them.

These compounds are excellent progestogens which are devoid of residual androgenic activity.

32 Claims, No Drawings

19-NOR-PREGNENE DERIVATIVES AND PHARMACEUTICALS CONTAINING SUCH DERIVATIVES

The invention relates to substituted 19-nor-pregnene derivatives, methods of making these compounds and pharmaceutical compositions containing them.

The compounds according to this invention have specific and powerful progestational properties, and are devoid of residual androgenic activity.

19-nor-pregnene derivatives substituted in position 1,2- have been described in the literature. For example, FR-A-1 525 916 relates to a method of preparing compounds of the formula:

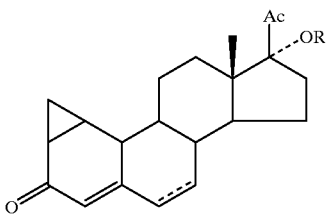

in which R is hydrogen or an acyl residue such as acetyl or hexanoyl.

In addition, 19-nor-pregnene derivatives substituted in position 6- are described in the following documents:

* FR-A-1 524 013 which relates to 3-enol ether pregnane derivatives obtained from the 4-pregnene-3,20-diones of the formula:

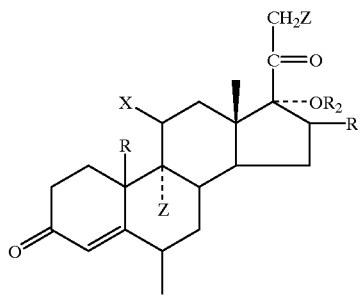

among which 6α-methyl-17α-hydroxy-4-pregnene-3,20-dione may be cited;

* DE-A-2 148 261 which describes a method of preparing 6α-methyl-19-nor-pregnenes of the formula:

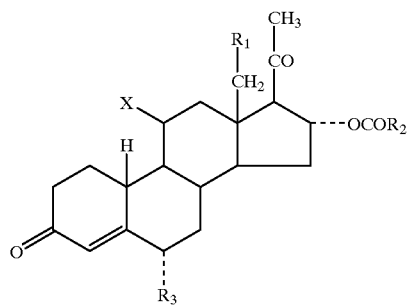

in which $R_1$ is hydrogen or methyl and $R_2$ is a $(C_1-C_9)$alkyl; or

* BE 757 285 which relates to pharmaceuticals containing 3,20-dioxo-6α-methyl-17α-acetoxy-19-nor-$\Delta^4$-pregnene.

19-nor-pregnene derivatives such as those described above usually exhibit however androgenic side effects.

On the other hand, the conversion of 17α,20-isopropylidenedioxy-4,5-seco-3-pregnyn-5-one to 6,6-dimethyl-17α-hydroxyprogesterone is disclosed in U.S. Pat. No. 3,891,677.

The Applicant has now found that 19-nor-pregnene derivatives which possess at least two substituents in position 1-, 2-, 1,2- and/or 6-, display a potent progestational activity while being devoid of residual androgenic activity.

A first aspect of this invention thus encompasses compounds having the structure represented by the following general formula (I):

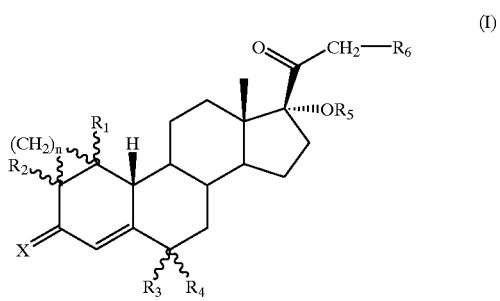

wherein:

$R_1$, $R_2$, $R_3$, $R_4$ and $R_6$ each independently represent hydrogen or a $(C_1-C_6)$alkyl, $R_5$ is hydrogen, a $(C_1-C_6)$alkyl or a —$COR_7$ group where $R_7$ is a $(C_1-C_6)$alkyl, n is zero or one, and X is oxygen or a hydroxyimino group, provided that when n=0, at least two of $R_1$, $R_2$, $R_3$ and $R_4$ are different from hydrogen and that when n=1, $R_3$ and $R_4$ are not simultaneously hydrogen.

As used herein, the term "alkyl" means a branched or linear saturated hydrocarbon radical, such as for example methyl, ethyl, propyl, isopropyl, butyl, isobutyl, t-butyl, pentyl and hexyl.

As used herein the group —$COR_7$ wherein $R_7$ is a $(C_1-C_6)$alkyl includes, for example, acetyl, propionyl, butyryl, isobutyryl, t-butyryl, valeryl and hexanoyl, acetyl being preferred.

Preferred compounds of formula (I) are those wherein $R_1$, $R_2$ and $R_6$ are hydrogen, $R_3$ and $R_4$ are a $(C_1-C_6)$alkyl, $R_5$ is a group —$COR_7$ and n is zero, those where X is oxygen being especially preferred. Also preferred are the compounds of formula (I) wherein $R_1$, $R_2$, $R_4$ and $R_6$ are hydrogen, $R_3$ is a $(C_1-C_6)$alkyl, $R_5$ is a group —$COR_7$ and n is one. Further preferred are the compounds of formula (I) wherein $R_4$ and $R_6$ are hydrogen, $R_3$ is a $(C_1-C_6)$alkyl, $R_5$ is a group —$COR_7$ and n is zero. Among the latter, those where $R_1$ is hydrogen and $R_2$ is a $(C_1-C_6)$alkyl and those where $R_1$ is a $(C_1-C_6)$alkyl and $R_2$ is hydrogen are also preferred, those where X is oxygen being especially preferred.

According to another aspect, the invention relates to a method of preparing the compounds of formula (I): they can be made following the reaction scheme below in which $R_1$, $R_2$, $R_3$, $R_4$, $R_5$, $R_6$, n and X have the same meaning as set forth above.

REACTION SCHEME
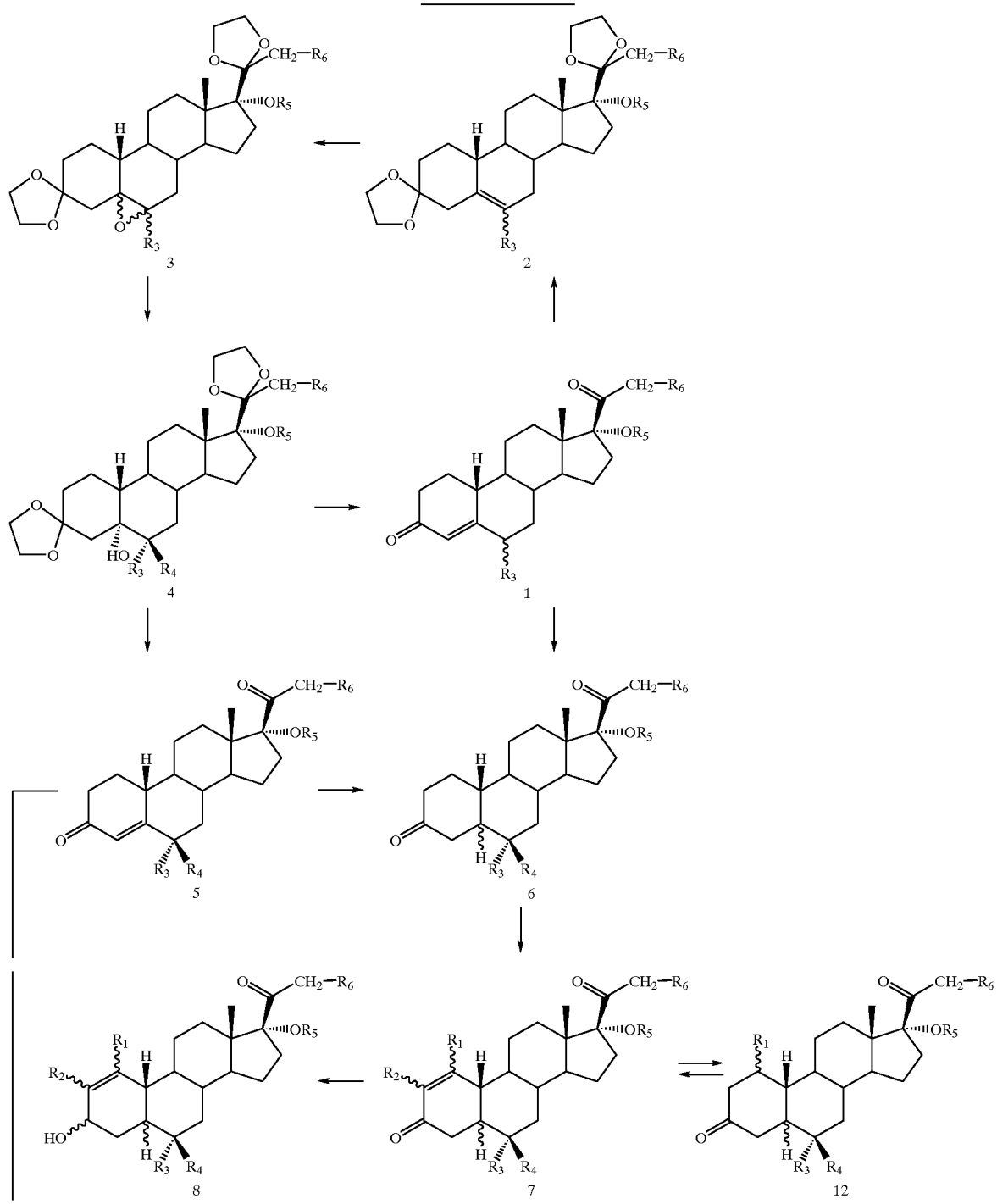

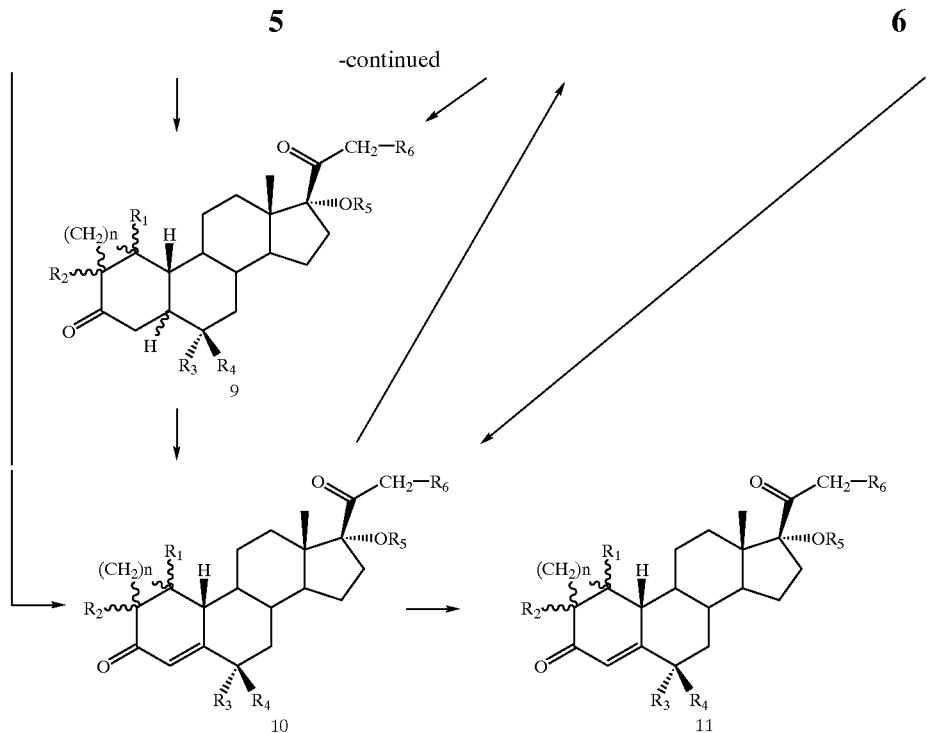

Compounds 5 where $R_3$ and $R_4$ are a $(C_1$–$C_6)$alkyl can be prepared as follows: Compounds 1 are prepared using a process similar to that described in DE-A-2 148 261. In the case where $R_5$=—$COR_7$, they are saponified by sodium hydroxide in a mixture of ethanol and tetrahydrofuran. Products 1 ($R_5$=H) are separated by precipitation in water followed by crystallization in an alcohol, preferably methanol or ethanol. Then, they are dissolved in toluene to which is added 1 to 10 molar equivalents of ethylene glycol, preferably 5 molar equivalents, triethylorthoformate and a catalytic amount of p-toluenesulfonic acid. The reaction mixture is stirred at a temperature of about 20° C. to 80° C., preferably 40° C. for about 2 to 8 hours. The reaction mixture is cooled and poured into iced water and extracted with a suitable organic solvent. The residue obtained after evaporation of the solvent can be purified by crystallization or by flash-chromatography to yield the compounds 2.

Treatment of compounds 2 with 3-chloroperoxybenzoic acid (MCPBA) in methylene chloride gives a mixture of 5,6-oxiranes 3 which are separated by crystallization or by flash-chromatography. Addition of an excess of $R_4$-magnesium-halide to the compounds 3 in tetrahydrofuran at a temperature of about 20° C. to 60° C. for about 8 hours, and treatment of the reaction mixture with a solution of ammonium chloride and extraction with toluene and evaporation of the solvent gives the compounds 4.

Deprotection followed by dehydration of the tertiary hydroxy group gives the compounds 5 which can be optionally esterified by known processes used for esterification in steroid chemistry or alkylated by an alkyl halide according to conventional methods of Williamson ether synthesis such as that described by B. G. Zupancic and M. Sopcic, *Synthesis*, 1979, 123 or by D. R. Benedict et al., *Synthesis*, 1979,428–9.

Compounds 6 where $R_3$ is $(C_1$–$C_6)$alkyl and $R_4$ is hydrogen can be prepared as follows:

Compounds 6 with the 5β-H configuration are obtained by hydrogenation of compounds 1 or 5 in tetrahydrofuran, acetic acid or an alcohol such as methanol, ethanol or propanol, with palladium or a palladium or platinium derivative.

Compounds 6 with the 5α-H configuration can be obtained by chemical reduction of compounds 1 or 5 with sodium dithionite using a procedure described by F. Camps et al., *Tetrahedron Lett.*, 1986, 42, n.16, 4603–4609 or R. S. Dhillon et al., *Tetrahedron Lett.*, 1995, 36, n.7, 1107–8.

The compounds of formula (I) can be obtained as follows:

Bromination followed by dehydrobromination of the compounds 6 according to well-known techniques (Y. J. Abul-Haij, *J. Org. Chem.*, 1986, 51, 3059–61; C. Djerassi and C. R. Scholz, *J. Am. Soc.*, 1948, 417; R. Joly et al, *Bull. Soc. Chim. Fr.*, 1957, 366) gives the compounds 7 ($R_1$=$R_2$=H).

Compounds 5 ($R_5$=H) can be transformed to their 20,20-ethanedioxy derivatives then converted to their 2-hydroxymethylene sodium salt and alkylated using an alkyl iodide such as methyl iodide, ethyl iodide or propyl iodide following the method described by N. W. Atwater et al. in *J. Org. Chem.*, 1961, 23, 3077–83 to obtain compounds 10 ($R_1$=H, $R_2$=alkyl, n=0).

Optionally, chemical reduction by hydrogenation of the 4,5-double bond of compounds 10 ($R_1$=H, $R_2$=alkyl, n=0), followed by bromination/dehydrobromination gives compounds 7 ($R_1$=H, $R_2$=alkyl).

Addition of a lithium dialkylcuprate $LiCu(R_1)_2$ or of the corresponding alkylmagnesium halide under copper catalysis (for example CuI, CuCl or CuCN) to compounds 7 ($R_1$=$R_2$=H) gives compounds 12 ($R_1$=alkyl) which can be converted to compounds 10 ($R_1$=alkyl, $R_2$=H, n=0) using well-known techniques for the introduction of a 4,5-double bond in steroid chemistry, or transformed to compounds 7 ($R_1$=alkyl, $R_2$=H) by dehydrogenation or by bromination/dehydrobromination. Compounds 12 can also be alkylated in position 2- by a similar process to obtain compounds 10 ($R_2$=alkyl, n=0) which are then converted to compounds 7 ($R_1$=$R_2$=alkyl) as described above.

Compounds 9 ($R_1$=H or alkyl, $R_2$=H or alkyl, n=1) are prepared by reaction of compounds 7 ($R_1$=H or alkyl, $R_2$=H or alkyl) with a dimethylsulfoxonium methylide produced by the reaction of trimethylsulfoxonium iodide (preferably with a base) with sodium hydride in tetrahydrofuran, dimethylformamide or dimethylsulfoxide. They can also be prepared by reaction of compounds 7 with diazomethane catalyzed by palladium or copper derivatives. Alternatively, compounds 7 ($R_1$=H or alkyl, $R_2$=H or alkyl) can be reduced with sodium borohydride in the presence of cerium chloride into compounds 8 ($R_1$=H or alkyl, $R_2$=H or alkyl) which are submitted to a Simmons-Smith reaction according to various known described procedures (H. E. Simmons and R. D. Smith, *J. Am. Chem. Soc.*, 1958, 80, 5323; H. E. Simmons and R. D. Smith, *J. Am. Chem. Soc.*, 1959, 81, 4256; *Org. Synthesis*, 1961, 41, 72; J. Furukawa et al., *Tetrahedron Lett.*, 1966, 3353; J. Furukawa et al., *Tetrahedron* 1968, 24, 53; S. E. Denmark and Edwards, *J. Org. Chem.*, 1991, 56, 6974–81).

Oxidation of the 3-hydroxy group of compounds 8 with various oxidizing agents such as $CrO_3$/pyridine gives compounds 9.

Compounds 9 ($R_1$=H or alkyl, $R_2$=H or alkyl, n=0 or 1) are converted to their silyl enol ether and dehydrogenated with palladium acetate in refluxing acetonitrile to give compounds 10. Alternatively, the 4,5-double bond can be introduced by bromination followed by dehydrobromination using a process similar to that described above for compounds 7. Condensation of compounds 10 with hydroxylamine hydrochloride in a mixture of dioxane and pyridine gives compounds 11.

The compounds according to this invention have specific and powerful progestational properties. Therefore they are useful for the treatment of a variety of endocrine-gynaecological disorders, related either to an oestrogen/progesterone imbalance, including menstrual disorders (spaniomenouhea, oligomenorrhea, secondary amenorrhea, premenstrual tension, headache, water retention, mood alteration), breast disorders (cyclical mastalgia, benign breast disease, breast tumors), endometrial diseases (hyperplasia, pre-malignant alteration tumors); or to conditions requiring inhibition of gonadotropiiagonadal sections: endometriosis, polycystic ovary syndrome in women, prostate diseases in men.

On the other hand, the compounds according to the invention can be used as contraceptive agents, either alone or in combination with an effective amount of sex steroid such as oestradiol, ethynyl oestradiol or testosterone, and again alone or in combination with an oestrogen for hormonal replacement therapy in postmenopausal women.

The progestational activity of the compounds according to the present invention can be assessed mainly in two specific experimental models the affinity for the progesterone receptor (PR) in vitro, and the endometrial tranformation of the rabbit uterus in vivo. Human PRs are readily available in high amounts from the T47-D cell line in culture (M. B. Mockus et al., *Endocrinology*, 1982, 110, 1564–1571). Relative binding affinities (RBA) for the human T47-D cell PR are determined as previously described (J. Botella et al., *J. Steroid Biochem. Molec. Biol.*, 1994, 50, 41–47) using [$^3$H]-ORG 2058 as a labelled specific ligand (G. Fleischmann and M. Beato, *Biochim. Biophys. Acta*, 1978, 540, 500–517) and nomegestrol acetate as a non-radioactive reference progestin. Competitive incubations were performed against 2 nM of [$^3$H]-ORG 2058 for 3 hours at 4° C. with six different concentrations of non-labelled steroid, chosen between 4 and 256 nM following a $½^n$ dilution scheme. Displacement curves were fitted for each experiment, and the concentration inhibiting 50% of the specific binding of [$^3$H]-ORG 2058 was calculated for each curve ($IC_{50}$).

TABLE 1

Relative binding affinity to human T47-Dcell progesterone receptor

| Progestin | $ED_{50}^{(a)}$ in nM | (n) | RBA |
|---|---|---|---|
| Nomegestrol acetate | 8.9 ± 2.0 | (8) | 100% |
| Compound of example 1 | 27.8 ± 2.0 | (4) | 32% |
| Compound of example 4 | 22.8 ± 1.7 | (4) | 39% |
| Compound of example 5 | 17.7 ± 2.4 | (4) | 50% |

(a) mean ± s.e.m.;
(n) number of experiments

One specific pharmacological test has been standardized in vivo for the detection and quantitation of pseudogestagenic activity since the mid-30's: it is based on the property of the uterus of estrogen-primed immature female rabbits to respond to very slight amounts of progestin by a typical endometrial transformation into a densely packed and interlaced epithelial network called "dentelle". The original test schedule, which includes 6 days of estrogen priming (total subcutaneous dose of 30 μg/rabbit of oestradiol benzoate) followed by 5 days of progestational treatment, was designed as early as 1930 by C. Clauberg, *Zentr. Gynäkol.* 1930, 54, 2757–2770. The semi-quantitative scale used to grade the intensity of the microscopical appearance of the dentelle was set up by M. K. McPhail, *J. Physiol* (London), 1934, 83, 145–156. This overall Clauberg-McPhail procedure has been extensively used to screen steroids for putative progestational activity in vivo and is still part of the basic hormonal profile of any new progestin such as norgestimate (A Phillips et al., *Contraception*, 1987, 36, 181–192), or desogestrel (J. Van der Vies and J. De Visser, *Arzneim. Forsch/Drug Res.*, 1983, 33, 231–236). The progestational potency is inversely related to the dose needed to induce a half-maximal stimulation of the dentelle, i.e. to record a mean McPhail grade equal to 2. This $ED_{50}$ is deduced from the dose-response curve and expressed in total dose/rabbit/5 days. All compounds were tested only following oral administration by gavage, in suspension in a carboxy-methylcellulose solution. The maximal dose administered was 1 mg, roughly corresponding to 5 times the $ED_{50}$ of nomegestrol acetate, a potent orally active 19-norprogesterone-derived progestin (J. Paris et al., *Arzneim. Forsch./Drug Res.*, 1983, 33, 710–715).

TABLE 2

Clauberg-McPhail test by oral administration (gavage)

| Progestin | $ED_{50}^{(a)}$ (μg/rabbit 5 days) | (n) | Relative activity |
|---|---|---|---|
| Nomegestrol acetate | 170 ± 41 | (5) | 100% |
| Example 1 | 152 ± 28 | (3) | 112% |
| Example 4 | 66 ± 11 | (2) | 258% |
| Example 5 | >750 ± 6.0 | (1) | >17% |

(a) mean ± s.e.m.;
(n) number of experiments

The residual androgenic potential is an important feature to be evaluated for any new progestin, because it is highly predictive of androgenic side-effects in women. One pharmacological model of androgenic activity has been standardized to screen steroids or related compounds in immature castrated male rats, using the hypertrophy of the vental prostate and of the seminal vesicle as the endpoint, following 10 daily administrations (R. I. Dorfman, in *Methods in Hormone Research*, volume 2, London, Academic Press, 1962: 275–313; A. G. Hilgar and D. J. Hummel, *Androgenic* and Myogenic Endocrine Bioassay Data, U.S. Department of Health, Education and Welfare, Washington D.C., 1964). Medroxyprogesterone acetate is a 6α-methylpregnene derivative which, besides its main progestational activity, is well-known for its weak androgenic properties (M. Tausk and J. de Visser, In *International Encyclopedia of Pharmacology and Therapeutics*, Section 48: Progesterone, Progestational Drugs and Antifertility Agents, volume II, OXFORD, Pergamon Press, 1972: 35–216); it was therefore chosen as a reference compound in the testing for residual androgenic activity of some compounds according to the invention.

Compounds of examples 1 and 4 were tested for residual androgenic activity in the immature castrated male rat model by gavage (PO), in comparison, respectively, with medroxyprogesterone acetate and cyproterone acetate (a 1,2α-cyclomethylene pregnene derivative with potent progestational activity); testosterone was used as a standard androgenic agent by subcutaneous injection (SC).

TABLE 3

Residual androgenic activity of the compound of example 1

| Steroid | Dose (mg/animal/day) | Ventral Prostate (mg) | Seminal Vesicle (mg) |
| --- | --- | --- | --- |
| Castrated controls | — | 12.0 ± 0.9 | 12.3 ± 0.7 |
| Testosterone, SC | 0.05 | 90.4 ± 4.4*** | 90.3 ± 6.7*** |
| Medroxyprogesterone acetate, PO | 20 | 29.1 ± 1.4*** | 19.9 ± 1.8** |
| Example 1, PO | 20 | 13.0 ± 0.3 ns | 10.4 ± 0.5 ns | mean ± s.e.m. of 8 animals per group ;
**p <0.01 and
***p <0.001
ns: not statistically different from controls.

TABLE 4

Residual androgenic activity of the compound of example 4

| Steroid | Dose (mg/animal/day) | Ventral Prostate (mg) | Seminal Vesicle (mg) |
| --- | --- | --- | --- |
| Castrated controls | — | 11.8 ± 0.6 | 10.4 ± 0.6 |
| Testosterone, SC | 0.05 | 80.9 ± 3.4*** | 79.0 ± 5.3*** |
| Cyproterone acetate, PO | 20 | 15.3 ± 1.3* | 11.3 ± 0.6 ns |
| Example 4, PO | 20 | 12.1 ± 0.4 ns | 11.2 ± 0.5 ns | mean ± s.e.m. of 7 or 8 animals per group;
*p <0.05 and
***p <0.001
ns: not statistically different from controls.

The compounds of examples 1 and 4 were totally inactive on the growth of male accessory sex organs (Tables 3 and 4). The stimulatory effect of cyproterone acetate was very weak and limited to the ventral prostate, at the border of statistical significance (Table 4), while medroxyprogesterone acetate caused both organs to more or less double in weight (Table 3).

Thus, the compounds according to the present invention are potent progestogens devoid of any residual androgenic activity.

Thus according to another aspect, the invention relates to pharmaceutical compositions containing an effective amount of a compound of formula (I), mixed with suitable pharmaceutically acceptable excipients. Said compositions may further comprise an effective amount of an oestrogen.

Another aspect of the invention comprises a method of treating or preventing endocrine—gynaecological disorders, and a method of inhibiting gonadotropic/gonadal secretions. The compounds according to the present invention can be administered at therapeutically effective dosage for each condition mentioned above. Administration of the active compounds described herein can be via any of the accepted modes of administration for agents used in similar indications.

The usual, necessary daily dose of the compound according to the invention will be in the range of 0.001 to 1 mg/kg of body weight per day of the active compound of formula (I). Most conditions respond to a treatment comprising a dosage level in the order of 0.002 to 0.2 mg/kg of body weight per day. Thus, for administration to a 50 kg person, the dosage range would be about 1 mg per day, preferably between about 0.1 to 10 mg per day.

Depending on the specific clinical status of the disease, administration can be made via any accepted systemic delivery system, for example, via oral route or parenteral route such as intravenous, intramuscular, subcutaneous or percutaneous route, or vaginal, ocular or nasal route, in solid, semi-solid or liquid dosage forms, such as for example, tablets, suppositories, pills, capsules, powders, solutions, suspensions, cream, gel, implant, patch, pessary, aerosols, collyrium, emulsions or the like, preferably in unit dosage forms suitable for easy administration of fixed dosages. The pharmaceutical compositions will include a conventional carrier or vehicle and a compound of formula (I) and, in addition, may include other medicinal agents, pharmaceutical agents, carriers, adjuvants, etc.

If desired, the pharmaceutical composition to be administered may also contain minor amounts of non-toxic auxiliary substances such as wetting or emulsifying agents, pH buffering agents and the like, such as for example, sodium acetate, sorbitan monolaurate, triethanolamine oleate, etc.

The compounds of this invention are generally administered as a pharmaceutical composition which comprises a pharmaceutical vehicle in combination with a compound of formula (I). The amount of the drug in a formulation can vary within the full range employed by those skilled in the art, e.g., from about 0.01 weight percent (wt %) to about 99.99 wt % of the drug based on the total formulation and about 0.01 wt % to 99.99 wt % excipient.

The preferred mode of administration, for the conditions mentioned above, is oral administration using a convenient daily dosage regimen which can be adjusted according to the degree of the complaint. For said oral administration, a pharmaceutically acceptable, non-toxic composition is formed by the incorporation of the selected compound of formula (I) in any of the currently used excipients, such as, for example, pharmaceutical grades of mannitol, lactose, starch, magnesium stearate, sodium saccharine, talc, cellulose, glucose, gelatin, sucrose, magnesium carbonate, and the like. Such compositions take the form of solutions, suspensions, tablets, pills, capsules, powders, sustained release formulations and the like. Such compositions may contain between 0.01 wt % and 99.99 wt % of the active compound according to this invention.

Preferably the compositions will have the form of a sugar coated pill or tablet and thus they will contain, along with the active ingredient, a diluent such as lactose, sucrose, dicalcium phosphate, and the like; a disintegrant such as starch or derivatives thereof; a lubricant such as magnesium stearate and the like ; and a binder such as starch, polyvinylpyriolidone, acacia gum, gelatin, cellulose and derivatives thereof, and the like. The invention is now illustrated by the examples below. In these examples, the following abbreviations are used:

s: singlet
d: doublet
t: triplet
q: quadruplet
m: multiplet
dd: doubled doublet
bs: broad singlet

EXAMPLE 1

17α-acetoxy-6,6-dimethyl-3,20-dioxo-19-nor-pregna-4-ene (5)

A/ 17α-hydroxy-6α-methyl-3,20-dioxo-19-nor-pregna-4-ene (1)

To a solution of 17α-acetoxy-6α-methyl-3,20-dioxo-19-nor-pregna-4-ene (100 g, 268 mmol.) in absolute ethanol and tetrahydrofuran (200 mL) was added, in 45 min. at room temperature, 1N sodium hydroxyde (300 mL, 300 mmol.). The solution was stirred (8 hours) and poured into iced water (4000 mL). The precipitate was filtered and dried at 50° C. under vacuum (yield: 70 g, 78.9%), mp: 172° C.

$^1$H-NMR (CDCl$_3$,δ): 0.79 (s, 3H); 1.25 (d, 3H); 2.29 (s, 3H); 2.68 (m, 1H); 5.87 (s, 1H).

B/ Bis-[3,3-20,20-ethanedioxy]-17α-hydroxy-6-methyl-19-nor-pregna-5-ene (2)

To a suspension of compound 1 (70 g, 211 mmol.) in anhydrous ethylene glycol (1000 mL), acetonitrile (700 mL) and triethylorthoformate (105 mL, 633 mmol.) was added para-toluenesulfonic acid monohydrate (5.25 g, 27.6 mmol.). The mixture was stirred (2 hours) and neutralizated by triethylamine (8 mL, 57.4 mmol.). After concentration to 1000 ml, the suspension was poured into water (4000 mL). The precipitate was filtered and dried at 60° C. under vacuum (yield: 81 g, 92.1%), mp: 214° C.

$^1$H-NMR (CDCl$_3$,δ): 0.85 (s, 3H); 1.40 (s, 3H); 1.65 (s, 3H); 2.80 (m, 1H); 4.00 (m, 8H).

C/ 5α,6α-epoxy-bis[3,3-20,20-ethanedioxy]-17α-hydroxy-6β-methyl-19-nor-pregnane (3)

To a solution of compound 2 (70 g, 167 mmol.) in methylene chloride (800 mL) was added a solution of MCPBA (43.29 g, 200.17 mmol., 80% pure) in methylene chloride (250 mL). The reaction mixture was stirred for 1 hour. The precipitate was filtered and the organic phase was washed with NaHSO$_3$ and with a solution of sodium hydrogen carbonate. The organic phase was dried (Na$_2$SO$_4$), concentrated and the residue was flash-chromatographed on silica gel using toluene/ethyl acetate as eluting solvent to give 20.3 g of the title compound (yield: 27.63%), mp: 220° C.

$^1$H-NMR (CDCl$_3$,δ): 0.80 (s, 3H); 1.25 (s, 3H); 1.35 (s, 3H); 4.00 (m, 8H).

D/ Bis[3,3-20,20-ethanedioxy]-5α,17α-dihydroxy-6,6-dimethyl-19-nor-pregnane (4)

To a solution of compound 3 (30 g, 69 mmol.) in tetrahydrofuran (1200 mL) was added 1.4 M methyl magnesium bromide in a tetrahydrofuran/toluene mixture (250 mL, 345 mmol.). The solution was stirred at reflux overnight. The mixture was poured into a mixture of ice and saturated ammonium chloride (1000 mL). The reaction mixture was extracted with toluene, washed by water and dried (Na$_2$SO$_4$). Evaporation of the solvent gave a residue which was chromatographed using toluene/ethyl acetate as eluting solvent (yield: 15.4 g, 49.55%), mp: 212° C.

$^1$H-NMR (CDCl$_3$,δ): 0.85 (s, 3H); 0.95 (s, 6H); 1.35 (s, 3H); 4.00 (m, 8H).

E/ 17α-acetoxy-6,6dimethyl-3,20-dioxo-19-nor-pregna-4-ene

To the above compound (30.8 g, 68.33 mmol.) in acetone (300 mL) and water (30 mL) was added para-toluenesulfonic acid monohydrate (1.33 g, 7 mmol.). The reaction mixture was stirred at room temperature for 5 hours. After neutralisation with NaHCO$_3$, the mixture was poured into iced water (100 mL) and extracted twice with methylene chloride. The organic layer was washed with water, dried (Na$_2$SO$_4$) and concentrated to give 24.3 g of 5α,17α-dihydroxy-6,6-dimethyl-3,20-dioxo-19-nor-pregnane (yield: 98.2%), mp: 224° C.

$^1$H-NMR (CDCl$_3$,δ): 0.75 (s, 3H); 0.91 (s, 3H); 1.08 (s, 3H); 2.29 (s, 3H).

To a solution of this compound (15 g, 41.20 mmol.) in acetic acid (120 mL) was added a few drops of H$_2$SO$_4$ (98%). The mixture was heated at 60° C. for 5 hours. Then, it was poured into a solution saturated with NaHCO$_3$ and extracted with methylene chloride. The organic phase was dried (Na$_2$SO$_4$) and evaporated to give 12.3 g of 17α-hydroxy-6,6-dimethyl-3,20-dioxo-19-nor-pregna-4-ene (yield 96.3%), mp: 172° C.

$^1$H-NMR (CDCl$_3$,δ): 0.79 (s, 3H); 1.15 (s, 6H); 2.09 (s, 3H); 5.97 (s, 1H).

To a solution of this compound (12.3 g, 35.7 mmol.) in acetic acid (120 mL) and acetic anhydride (70 mL) was added para-toluenesulfonic acid (25 g, 13.2 mmol.). The mixture was stirred for 12 hours at room temperature. After completion of the reaction, the excess of anhydride was decomposed by water. The mixture was extracted with methylene chloride and washed with a 1N aqueous NaOH solution. The organic phase was dried (Na$_2$SO$_4$) and concentrated. The residue was flash-chromatographed using toluene/ethyl acetate as eluting solvent and recrystallized in diisopropyl ether (yield: 7 g, 50.81%), mp: 200° C.

$^1$H-NMR (CDCl$_3$,δ): 0.71 (s, 3H); 1.18 (s, 6H); 2.05 (s, 3H); 2.11 (s, 3H); 5.99 (s, 1H).

EXAMPLES 2 AND 3

17α-acetoxy-6β-ethyl-6α-methyl-3,20-dioxo-19-nor-prega-4-ene (5.a) and 17α-acetoxy-6β-propyl-6α-methyl-3,20-dioxo-19-nor-pregna-4-ene (5.b)

Starting from compound 3 using the process described for compound 5 but replacing the methyl magnesium bromide by ethyl or propyl magnesium bromide the following compounds were obtained: 17α-acetoxy-6β-ethyl-6α-methyl-3,20-dioxo-19-nor-pregna-4-ene, mp: 160° C. (example 2), $^1$H-NMR (CDCl$_3$,δ) 0.7 (s, 3H); 0.72 (t, 3H); 1.08 (s, 3H); 2.05 (s, 3H); 2.11 (s, 3H); 5.95 (s, 1H); and 17α-acetoxy-6β-propyl-6α-methyl-3,20-dioxo-19-nor-pregna-4-ene (example 3).

EXAMPLE 4

17α-acetoxy-1α,2α-methylene-6α-methyl-3,20-dioxo-19-nor-pregna-4-ene (10)

A$_1$/ 17α-acetoxy-6α-methyl-3,20-dioxo-19-nor-pregnane (6)

To a solution of 17α-acetoxy-6α-methyl-3,20-dioxo-19-nor-pregna-4-ene (10 g, 26.84 mmol.) in dioxane (100 mL)

and water (100 mL) containing NaHCO$_3$ (14.65 g, 174.46 mmol.) was added sodium dithionite (7.9 g, 38.5 mmol.) and the reaction mixture was stirred at 50° C. for 1 hour, during which time additional sodium dithionite was added in three portions of 7.9 g each. The reaction mixture was cooled to room temperature and cold water was added until the solution became clear. Thereafter, the solution was extracted with diethyl ether, dried (Na$_2$SO$_4$), concentrated under vacuum and flash-chromatographed (toluene/ethyl acetate) to give 2 g of compound 6 (yield: 20%), mp: 202° C.

$^1$H-NMR (CDCl$_3$, δ): 0.65 (s, 3H); 0.86 (d, 3H); 2.03 (s, 3H); 2.09 (s, 3H); 231 (m, 3H); 2.62 (m, 1H); 2.90 (m, 1H).

B$_1$/ 17α-acetoxy-6α-methyl-3,20-dioxo-19-nor-pregna-1-ene (7)

A mixture of compound 6 (20 g, 53.40 mmol.) and Pd(OAc)$_2$ (14.38 g, 64.05 mmol.) in acetonitrile (300 mL) was refluxed for 8 hours. After cooling, the palladium was filtered off and the solvent evaporated. The residue was flash-chromatographed on silica gel using toluene/ethyl acetate (8/2) as eluting solvent to give 7 g of compound 7 (yield: 35%), mp: 186–188° C.

$^1$H-NMR (CDCl$_3$, δ): 0.69 (s, 3H); 0.93 (d, 3H); 2.07 (s, 3H); 2.12 (s, 3H); 2.76 (d, 1H); 2.94 (m, 1H); 6.02 (dd, 1H); 7.11 (dd, 1H).

C$_1$/ 17α-acetoxy-1α,2α-methylene-6α-methyl-3,20-dioxo-19-nor-pregnane (9)

To a stirred suspension of trimethylsulfoxonium iodide (7.68 g, 34.91 mmol.) in dimethyl sulfoxide (50 mL) was added sodium hydride in oil (60%) (153 g, 382 mmol.). The mixture was stirred at 25° C. for 1 hour, and then compound 7 (2.97 g, 7.98 mmol.) was added. After 3 hours, the reaction mixture was poured in water. Collection of the resulting solid by filtration and flash-chromatography on silica gel using toluene/ethyl acetate as eluting solvent gave 1 g of compound 9 (yield: 33%), mp: 204° C.

$^1$H-NMR (CDCl$_3$, δ): 0.68 (s, 3H); 0.84 (d, 3H); 2.02 (s, 3H); 2.12 (s, 3H); 2.52 (dd, 1H); 2.92 (m, 1H).

D$_1$/ 17α-acetoxy-1,α2α-methylene-6α-methyl-3,20-dioxo-19-nor-pregna-4-ene

To a solution of compound 9 (4 g, 10.35 mmol.) in tetrahydrofuran (80 mL) was added portionwise pyridinium tribromide (3.83 g, 1138 mmol.). After 30 min. the mixture was filtered, evaporated and the residue extracted with methylene chloride, washed with water and dried (Na$_2$SO$_4$). Evaporation of the solvent gave 5 g of a brown oil to which dimethylformamide (80 mL), Li$_2$CO$_3$ (1.53 g, 20.70 mmol.) and LiBr (0.90 g, 10.35 mmol.) were added. The mixture was heated at 140° C. for 1 hour. After cooling the salts were removed by filtration and the solvent concentrated under reduced pressure. The residue was extracted with methylene chloride, washed with water and dried on Na$_2$SO$_4$. Flash-chromatography on silica gel using toluene/ethyl acetate as eluting solvent gave 2 g of the title compound (yield: 50%), mp: 210° C.

$^1$H NMR (CDCl$_3$,δ) : 0.71 (s, 3H); 1.09 (d, 3H); 2.04 (s, 3H); 2.12 (s, 3H); 2.42 (m, 1H); 2.84 (m, 1H); 5.65 (s, 1H).

A$_2$/ Alternatively, compound 10 can also be prepared from 17α-acetoxy-6α-methyl-3,20-dioxo-19-nor-5β-pregnane obtained from hydrogenation of 17α-acetoxy-6α-methyl-3, 20-dioxo-19-nor-pregna-4-ene in acetic acid using Pd(OH)$_2$ as catalyst B$_2$/ Then, to a cooled solution of the resulting compound (20 g, 53 mmol.) in THF (200 mL) was added 17.1 g (53 mmol.) of pyridinium tribromide. After 2 hours the mixture was filtered, poured into iced water and extracted with methylene chloride. Evaporation of the solvent gave 23.8 g (yield: 98.3%) of crude 17α-acetoxy-2α-bromo-6α-methyl-3,20-dioxo-19-nor-5β-pregnane which was dehydrobrominated following the conditions described above in step D$_1$ to give 15.9 g (yield: 80%) of 17α-acetoxy-6α-methyl-3,20-dioxo-19-nor-5β-pregna-4-ene (7.a), mp: 184.C.

$^1$H-NMR (CDCl$_3$, δ): 0.69 (s, 3H); 0.9 (d, 3H); 2.02 (s, 3H); 2.1 (s, 3H); 2.9 (m, 1H); 6.02 (d, 1H).

C$_2$/ 17α-acetoxy-3α-hydroxy-6α-methyl-20-oxo-19-nor-5β-H-pregna-1-ene (8.a)

To 10 g (27 mmol.) of the compound obtained in step B$_2$ and 12 g of cerium chloride heptahydrate in methanol (200 mL) cooled to 0° C. were added, portionwise, 2.5 g (54 mmol.) of sodium borohydride. Then, the mixture was stirred for 1 hour at room temperature, poured into iced water and the precipitate collected by filtration, dried and recrystallized from diisopropyl ether to give 3.6 g of 8 (yield: 35.6%), mp: 211° C.

$^1$H-NMR (CDCl$_3$, δ): 0.65 (s, 3H); 0.92 (d, 3H); 2.0 (s, 3H); 2.1 (s, 3H) 2.9 (m, 1H); 4.32 (m, 1H); 5.64 (d, 1H); 5.96 (dd, 1H).

D$_2$/ 17α-acetoxy-1α,2α-methylene-6α-methyl-3,2-dioxo-19-nor-5β-pregnane (9.a)

To 3 g (80 mmol.) of compound 8.a in dichloroethane (200 mL) at −25° C. were added dropwise 40 mL of a 1N solution of diethyizinc in hexane followed by 6.45 mL of diiodomethane. After 1 night at room temperature, the white mixture was poured in a solution of ammonium chloride and extracted with methylene chloride. Evaporation of the solvent gave a residue which was flash-chromatographed on silica gel using toluene/ethyl acetate as eluting solvent to give 1.43 g of the 3α-hydroxy-1α,2α-methylene derivative.

$^1$H-NMR (CDCl$_3$, δ): 0.4 (m, 2H); 0.68 (s, 3H); 0.85 (d, 3H); 2.05 (s, 3H); 2.16 (s, 3H); 2.9 (m,1H); 4.13 (m, 1H).

Oxidation of the 3α-hydroxy-1α,2α-methylene derivative in acetone with Jones' reagent gave 1 g of 9.8 (70% yield) which was converted to 10 by the same procedure than that described in step D$_1$.

EXAMPLE 5

17α-acetoxy-1α,2β-methylene-6α-methyl-3,20-dioxo-19-nor-pregna-4-ene (10.a)

A/ 17α-acetoxy-6α-methyl-3,20-dioxo-19-nor-5β-pregnane (6.a)

Compound 1 (20 g, 53.69 mmol.) in methanol (200 mL) containing acetic acid (5 mL) and 20% Pd(OH)$_2$ (200 mg) on charcoal is hydrogenated under 1 atm. of H$_2$. Filtration of the catalyst and removal of the solvent followed by crystallization in ethyl acetate gave 12.06 g of compound 6.a (yield: 60%), mp: 204° C.

$^1$H-NMR (CDCl$_3$, δ): 0.63 (s, 3H); 0.80 (d, 3H); 2.01 (s, 3H); 2.10 (s, 3H); 2.91 (m, 1H)

B/ 17α-acetoxy-6α-methyl-3,20-dioxo-19-nor-5β-pregna-4-ene (7a)

Compound 7.a was prepared in 30% yield following the procedure described in example 4, step B$_2$, mp: 184° C.

$^1$H-NMR (CDCl$_3$, δ): 0.68 (s, 3H); 0.92 (d, 3H); 2.03 (s, 3H); 2.09 (s, 3H); 2.92 (m, 1H); 6.03 (d, 1H); 7.16 (dd, 1H).

C/ 17α-acetoxy-1β,2β-methylene-6α-methyl-3,20-dioxo-19-nor-5β-pregnane (9.b)

Compound 9.b was prepared in 30% yield following the procedure described in example 4, steps C$_1$ and D$_1$, mp: 174–176° C.

$^1$H-NMR (CDCl$_3$, δ): 0.61 (s, 3H); 0.79 (d, 3H); 2.01 (s, 3H); 2.11 (s, 3H); 2.88 (m, 1H).

D/ 17α-acetoxy-1β,2β-methylene-6α-methyl-3,20-dioxo-19-nor-pregna-4-ene

This compound was prepared in 19% yield following the procedure described in example 4, step D$_1$, mp: 247° C.

IR (KBr, cm$^{-1}$): 1730 vC=O; 1720 vC=O; 1644 vC=O; 1458 vC=C.

$^1$H-NMR (CDCl$_3$, δ): 0.59 (s, 3); 0.94 (d, 3H); 1.95 (s, 3H); 2.00 (s, 3H); 2.37 (d, 1H); 2.82 (m, 1H); 5.52 (s, 1H)

EXAMPLES 6 AND 7

17α-acetoxy-1β,2β-methylene-3E-hydroxyimino-6α-methyl-20-oxo-19-nor-pregna-4-ene (11) and 17α-acetoxy-1β,2β-methylene-3Z-hydroxyimino-6α-methyl-20-oxo-19-nor-pregna-4-ene (11.a)

To a solution of compound 10a (1.24 g, 3.25 mmol.) in dioxane (50 mL) were added successively hydroxylamine hydrochloride (0.45 g, 6.46 mmol.) and pyridine (3.1 mL). The mixture was heated to reflux for 15 hours. Then, the reaction mixture was poured into iced water and acidified with a 1N HCl solution. Extraction with methylene chloride and evaporation of the solvent gave 1.29 g of a crude product which was flash-chromatographed using toluene/ethyl acetate as eluting solvent.

The first product eluted was the E isomer and crystallized from ethanol (0.3 g, yield: 28.8%), mp: 172° C (example 6).

$^1$H-NMR (CDCl$_3$, δ): 0.5 (q, 1H); 0.65 (s, 3H); 1.02–1.04 (d, 3H); 2.05 (s, 3H); 2.12 (s, 3H); 2.95 (m, 2H); 5.62 (s, 1H).

The second product eluted was the Z isomer and it was crystallised from a mixture of absolute ethanol and diisopropyl ether (0.080 g, yield: 7.7%), mp: 168° C. (example 7).

$^1$H-NMR (CDCl$_3$, δ): 0.681 (s, 3H); 1.08–1.1 (d, 3H); 2.05 (s, 3H); 2.12 (s, 3H); 2.95 (m, 1H); 6.32 (s, 1H).

EXAMPLE 8

17α-acetoxy-2α,6α-dimethyl-3,2-dioxo-19-nor-pregna-4-ene (10.b)

A solution of 20,20-ethanedioxy-17α-hydroxy-6α-methyl-19-nor-pregna-4-ene (prepared from compound 5, R$_3$=CH$_3$, R$_5$=H, R$_6$=H, R$_4$=H) (10 g, 26.7 mmol.), sodium methoxide (8.25 g, 152.2 mmol.) and ethyl formate (12.71 g, 171.6 mmol.) was stirred at room temperature for 4 hours. Then, the precipitate was filtered, washed with diethyl ether to yield 11 g of the crude 2-hydroxymethylene sodium salt derivative which was used without further purification.

To this compound (11 g) in acetone (180 mL) were added potassium carbonate (135 g, 98 mmol.) and methyl iodide (46.4 g, 326.8 mmol.) and the mixture was stirred at room temperature for 12 hours. After filtration, the organic solution was poured into a solution of 1N NaOH, extracted with methylene chloride, dried (Na$_2$SO$_4$) and concentrated under vacuum to give a crude product (12.70 g) to which was added methanol (70 mL) and a solution of 6.66 g (166.5 mmol.) of sodium hydroxyde in water (6.6 mL) and the solution was refluxed for 5 hours. After cooling, the mixture was acidified to pH=1 with a solution of 1N HCl and then, poured into water. The precipitate was collected, washed with water and dried. Flash-chromatography on silica gel (toluene/ethyl acetate) gave 4.10 g of the 17α-hydroxy derivative of the title compound (yield: 40%).

$^1$H-NMR (CDCl$_3$, δ): 0.78 (s, 3H); 1.10 (d, 6H); 2.27 (s, 3H); 2.68 (t, 1H); 2.83 (s, 1H); 5.87 (s, 1H).

It was converted to its acetyl derivative following the procedure described for compound 6.a in 30% yield, mp: 144° C.

$^1$H-NMR (CDCl$_3$, δ): 0.7 (s, 3H); 1.13 (d, 6H); 2.06 (s, 3H); 2.12 (s, 3H); 2.95 (t, 1H); 5.88 (bs, 1H).

EXAMPLE 9

17α-acetoxy-1α,6α-dimethyl-3,20-dioxo-19-nor-pregn-4-ene (10.c)

A/ 17α-acetoxy-1α,6α-dimethyl-3,20-dioxo-19-nor-pregnane (12)

To a suspension of copper chloride (1.59 g, 16.11 mmol.) in tetrahydrofuran (400 mL) at 0° C. under N$_2$ was added slowly methyllithium (1.6 N) in diethyloxide (28.76 ml, 32.21 mmol.). After 1 hour, a solution of compound 7 (5 g, 13.42 mmol.) in tetrahydrofuran (40 mL) was added to the mixture at 0° C. After 6 hours, a saturated solution of ammonium chloride was carefully added dropwise over 10 min. This mixture was stirred for 15 min., then extracted with dichloromethane. The organic layer was dried (MgSO$_4$) and concentrated. The resulting crude product was flash-chromatographed (toluene/ethyl acetate) to give 3 g of 12 (yield: 57%), mp: 183° C.

$^1$H-NMR (CDCl$_3$, δ): 0.66 (s, 3H); 0.81 (d, 3H); 0.86 (d, 3H); 2.01 (s, 3H); 2.10 (s, 3H); 2.90 (t, 1H).

B/ Using the same procedure than that described for the preparation of compound 10 from compound 9, compound 10.c was obtained in 35% yield, mp: 209° C.

$^1$H-NMR (CDCl$_3$, δ): 0.81 (s, 3H); 0.90 (d, 3H); 1.15 (d, 3H); 2.06 (s, 3H); 2.12 (s, 3H); 2.95 (t, 1H); 5.95 (s, 1H).

EXAMPLE 10

17α-acetoxy-1β,6α-dimethyl-3,20-dioxo-19-nor-pregna-4-ene (10.d)

A/ 17α-acetoxy-1β,6α-dimethyl-3,20-dioxo-19-nor-5β-pregnane (12a)

Compound 12.a was prepared in 60% yield following the procedure described for compound 12, mp: 142° C.

$^1$H-NMR (CDCl$_3$, δ): 0.66 (s, 3H); 0.83 (d, 3H); 0.98 (d, 3H); 2.06 (s, 3H); 2.14 (s, 3H); 2.92 (t, 1H).

B/ Using the same procedure than that described for the preparation of compound 10 from compound 9, compound 10.d was obtained in 40% yield, mp: 187° C.

$^1$H-NMR (CDCl$_3$, δ): 0.69 (s, 3H); 1.06 (d, 3); 1.09 (d, 3H); 2.06 (s, 3H); 2.12 (s, 3H); 2.97 (m, 1H); 5.77 (s, 1H).

EXAMPLE 11

17α-acetoxy-1,2α-methylene-6,6-dimethyl-3,20dioxo-19-nor-pregna-4-ene (10.e)

This compound was prepared following the procedure described in Example 4 for compound 10; mp: 251.5° C.

$^1$H-NMR (CDCl$_3$, δ): 0.75 (s, 3H); 1.12 (d, 6); 2.03 (s, 3H); 2.11 (s, 3H); 2.65 (m, 1H); 2.95 (m, 1H); 5.25 (s, 1H).

The following examples illustrate the preparation of representative pharmaceutical formulations containing a compound of formula (I):

For oral administration

EXAMPLE 12

Tablets with delayed release.
Unit formulation for various dosages:

| | |
|---|---|
| Compound of formula (I) | 0.50 to 10.00 mg |
| Aerosil ® 200 | 0.37 to 0.50 mg |
| Precirol ® ATO 5 | 1.85 to 2.25 mg |
| Methocel ® E4 | 55.00 to 70.00 mg |
| Avicel PH ®101 | 10.00 to 20.00 mg |
| Lactose qs for 1 tablet of | 185.00 to 200.00 mg |

EXAMPLE 13

Fast release tablets.
Unit formulation for various dosages:

| | |
|---|---|
| Compound of formula (I) | 0.50 to 10.00 mg |
| Acrosil ® 200 | 0.37 to 0.50 mg |
| Precirol ® ATO 5 | 1.85 to 2.50 mg |
| Avicel ® PH 102 | 50.00 to 70.00 mg |
| Explotab ® or polyplasdone ® XL | 5.00 to 25.00 mg |
| Lactose qs for 1 tablet of | 185.00 to 200.00 mg |

EXAMPLE 14

Tablets.
Unit formulation for various dosages:

| | |
|---|---|
| Compound of formula (I) | 0.50 to 10.00 mg |
| Aerosil ® 200 | 0.30 to 0.50 mg |
| Compritol ® | 1.50 to 3.00 mg |
| Avicel ®PH 101 | 55.00 to 70.00 mg |
| Lactose qs for 1 tablet of | 185.00 to 200.00 mg |

Capsules.
Unit formulation for various dosages:

| | |
|---|---|
| Compound of formula (I) | 0.50 to 10.00 mg |
| Oleic acid qs for 1 capsule of | 250.00 to 260.00 mg |

Coating: gelatine, preservatives, glycerol

For vaginal administration

EXAMPLE 15

Vaginal gynaecologic capsule.
Unit formulation for a capsule:

| | |
|---|---|
| Compound of formula (I) | 0.50 to 15.00 mg |
| Vaseline | 150.00 to 200.00 mg |
| Sorbitol sesquioleate | 150.00 to 200.00 mg |
| Synthetic perhydrosqualene qs for 1 capsule of 1.85 g | |

Coating: gelatine, glycerol, preservatives for a soft capsule weighing 255 g

EXAMPLE 16

Vaginal suppository.
Unit formulation for a suppository:

| | |
|---|---|
| Compound of formula (I) | 0.50 to 15.00 mg |
| Witepsol ® H35 or H37 qs for a suppository of 3.00 g | |

EXAMPLE 17

Slow release vaginal suppository.
Unit formulation for a suppository of 3.00 g:

| | |
|---|---|
| Compound of formula (I) | 0.50 to 30.00 mg |
| Witepsol ® H19 or H35 | 1.00 to 1.30 g |
| Suppocire ® BM or NAI50 | 1.00 to 1.50 g |
| Precirol ® | 0.00 to 0.20 g |

For cutaneous or gynaecologic use

EXAMPLE 18

Bioadhesive gel for cutaneous or gynaecologic use.
Formula for 100 g:

| | |
|---|---|
| Compound of formula (I) | 0.10 to 1.00 g |
| Polyethylene glycol | 0.00 to 6.00 g |
| Transcutol ® | 0.00 to 6.00 g |
| Carboxypolyvinyl polymer | 0.50 to 1.00 g |
| Preservatives | 0.30 mg |
| Triethanolamine qs pH 6.5 | |
| Purified water qs for 100 g | |

EXAMPLE 19

Gel for cutaneous use.
Formula for 100 g:

| | |
|---|---|
| Compound of formula (I) | 0.10 to 2.00 g |
| Polyethylene glycol or Transcutol ® | 1.00 to 4.00 g |
| Ethyl alcohol | 20.00 to 40.00 g |
| Carboxypolyvinyl polymer | 0.50 to 2.00 g |
| Triethanolamine qs pH 6.5 | |
| Purified water qs for 100 g | |

EXAMPLE 20

Patches.
Content of the reservoir or matrix.
Preparation for 100 g:

| | |
|---|---|
| Compound of formula (I) | 0.25 to 20.00 mg |
| Enhancer* | 0.20 to 0.50 g |
| Suspending agent (HPMC** or Aerosil ®) | 0.10 to 1.00 g |
| Ethyl alcohol or silicone oil qs for 100 g | |

*enhancer: isopropyl palmitate, propyleneglycol, menthol, azone, N,N-dimethyl-acetamide, mono- or disubstituted pyrrolidone derivatives;
** HPMC: hydroxypropylmethylcellulose For percutaneous administration

EXAMPLE 21

Implants.
Formulation for 100 g of material to be extruded:

| | |
|---|---|
| Compound of formula (I) | 1.00 to 5.00 g |
| Polymers (EVA, polyorthocarbonates, silicone-based polymers) qs for 100 g | |

The temperature of the mixture shall not excede 150° C. in order not to impair the active ingredient.
Implants with reservoir.
The implant is a sealed silicone tubing of 2.5 to 3.5 cm long, 0.4 to 0.8 mm thick and 1.40 to 2 mm in diameter. The preparation is formulated as a suspension as follows:
For 100 g of suspension:

| | |
|---|---|
| Compound of formula (I) | 30.00 to 50.00 g |
| Suspending agent qs for 100 g | |

50 mg of the suspension for one implant.

EXAMPLE 22

Injectable depot.
Unit formulation for a flask of 5 ml:

| | |
|---|---|
| Compound of formula (I) | 10.00 to 50.000 mg |
| Polyethylene glycol 4000 | 100.00 to 200.000 mg |
| Preservatives | 0.006 mg |
| Sodium chloride and citrate | 0.150 mg |
| Distilled water for injection qs for 5.00 ml | |

EXAMPLE 23

Injectable suspension.
Unit formulation for a 2 ml ampoule:

| | |
|---|---|
| Compound of formula (I) | 5.00 to 10.00 mg |

Suspension solution:

| | |
|---|---|
| Polysorbate ® 80 | 0.045 g |
| Sodium carboxymethylcellulose | 0.010 g |
| Sodium chloride | 0.010 g |
| Purified water for injection qs for 2.00 ml | |

EXAMPLE 24

Intra-uterine device with reservoir.
Device with a silicone reservoir 2.5 to 35 cm long and 0.4 to 0.8 mm thick. The preparation is formulated as a suspension as follows:

For 100 g of suspension:

| | |
|---|---|
| Compound of formula (I) suspended in: | 0.60 to 1.00 g |
| Suspending agent (Aerosil ® or HPMC) | 0.50 g |
| Synthetic perhydrogenalene qs for 100 g | |

EXAMPLE 25

Bioadhesive gynaecological foam.
Formula for a dispenser of 50 g and a spray valve (2 ml)

| | |
|---|---|
| Compound of formula (I) | 0.10 to 0.25 g |
| Carboxypolyvinyl polymer | 0.50 to 1.00 g |
| Isobutane | 5.00 to 10.00 g |
| Excipient base F25/1 qs for 50.00 g | |

Shake the suspension before use.
Dispensed dosage from 2.00 to 10.00 mg
For nasal administration

EXAMPLE 26

Nasal suspension.
Formulation for 100 g of suspension:

| | |
|---|---|
| Compound of formula (I) | 5.00 to 50.00 mg |
| Aerosil ® PH 101 | 10.00 to 20.00 mg |
| Sodium carboxymethylcellulose | 5.00 to 50.00 mg |
| Phenylethyl alcohol | 2.00 to 10.00 mg |
| Polysorbate ® 80 | 10.00 to 20.00 mg |
| Purified water qs for 100 g | |

Shake the suspension before use
Dispensed dosage from 0.5 to 2.5 mg
For ophthalmic administration

EXAMPLE 27

Ophthalmic solution (collyrium).
Formulation for 100 g of solution. Container of 5 ml with glass droppers:

| | |
|---|---|
| Compound of formula (I) | 0.50 to 1.00 g |
| Glycerol | 5.00 g |
| Polyvidone or sodium chloride | 0.50 to 0.90 g |
| Sorbitol | 4.00 g |
| Preservatives (benzalkonium chloride or Cetrimide ®) | 0.01 g |
| EDTA | 0.01 g |
| Distilled water qs for 100 g | |

The solution is a sterile aqueous solution; it may contain stabilisers and antimicrobial agents.
The recommended dose is one drop four times daily.

EXAMPLE 28

Ophthalmic gel.
Formulation for 100 g of gel. Container: collapsible tube:

| | |
|---|---|
| Compound of formula (I) | 0.50 to 2.00 g |
| Cetrimide ® | 0.1 g |
| Sorbitol | 4.00 g |
| EDTA | 0.01 g |
| Carboxypolyvinyl polymer (Carbopol ® 971) | 0.14 to 0.20 g |
| Sodium hydroxyde 10% qs pH 6.5 | |
| Purified water qs for 100 g. | |

The sterile aqueous gel is filled in collapsible tubes.

The recommended dose is one drop one or two times daily.

Typical examples of the compounds of formula (1) provided by this invention include:

17α-acetoxy-6,6-dimethyl-3,2-dioxo-19-nor-pregna-4-ene
17α-acetoxy-6β-ethyl-6α-methyl-3,20-dioxo-19-nor-pregna-4-ene
17α-acetoxy-6β-propyl-6α-methyl-3,20-dioxo-19-nor-pregna-4-ene
17α-acetoxy-1α,2α-methylene-6α-methyl-3,20-dioxo-19-nor-pregna-4-ene
17α-acetoxy-1β,2β-methylene-6α-methyl-3,20-dioxo-19-nor-pregna-4-ene
17α-acetoxy-1β,2β-methylene-3E-hydroxyimino-6α-methyl-20-oxo-19-nor-pregna-4-ene
17α-acetoxy-1β,2β-methylene-3Z-hydroxyimino-6α-methyl-20-oxo-19-nor-pregna-4-ene
17α-acetoxy-2α,6α-dimethyl-3,20-dioxo-19-nor-pregna-4-ene
17α-acetoxy-1α,6α-dimethyl-3,20-dioxo-19-nor-pregna-4-ene
17α-acetoxy-1β,6α-dimethyl-3,20-dioxo-19-nor-pregna-4-ene
17α-acetoxy-1,2α-methylene-6,6-dimethyl-3,20-dioxo-19-nor-pregna-4-ene

What is claimed is:

1. A compound of the formula (I):

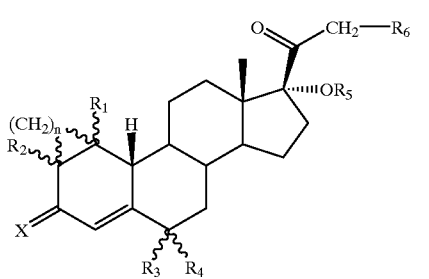

(I)

wherein:
$R_1$, $R_2$, $R_3$ and $R_4$ each independently represent hydrogen or a $(C_1-C_6)$alkyl,
$R_5$ is a —$COR_7$ group where $R_7$ is methyl,
$R_6$ is hydrogen,
n is zero, and
X is oxygen or a hydroxyimino group,
provided that at least two of $R_1$, $R_2$, $R_3$ and $R_4$ are different from hydrogen.

2. A compound according to claim 1, wherein $R_1$ and $R_2$ are hydrogen, and $R_3$ and $R_4$ are a $(C_1-C_6)$alkyl.

3. A compound according to claim 1, wherein $R_4$ is hydrogen, and $R_3$ is a $(C_1-C_6)$alkyl.

4. A compound according to claim 3, wherein $R_1$ is hydrogen and $R_2$ is a $(C_1-C_6)$alkyl.

5. A compound according to claim 3, wherein $R_2$ is hydrogen and $R_1$ is a $(C_1-C_6)$alkyl.

6. A compound according to claim 4, wherein X is oxygen.

7. A compound according to claim 5, wherein X is oxygen.

8. A pharmaceutical composition containing an effective amount of a compound according to claim 1, and a suitable excipient.

9. A pharmaceutical composition according to claim 8, containing from 0.01 to 99.99 weight % of the compound of formula (I).

10. A pharmaceutical composition according to claim 8, which is a contraceptive composition, further containing an effective amount of a sex steroid.

11. A pharmaceutical composition containing (i) a therapeutically effective amount of a compound according to claim 2 and (ii) a suitable excipient.

12. A pharmaceutical composition containing (i) a therapeutically effective amount of a compound according to claim 3 and (ii) a suitable excipient.

13. A pharmaceutical composition containing (i) a therapeutically effective amount of a compound according to claim 4 and (ii) a suitable excipient.

14. A pharmaceutical composition containing (i) a therapeutically effective amount of a compound according to claim 5 and (ii) a suitable excipient.

15. A pharmaceutical composition containing (i) a therapeutically effective amount of a compound according to claim 6 and (ii) a suitable excipient.

16. A pharmaceutical composition containing (i) a therapeutically effective amount of a compound according to claim 7 and (ii) a suitable excipient.

17. A pharmaceutical composition according to claim 8, which further contains a therapeutically effective amount of an estrogen.

18. The compound according to claim 1, which is 17α-acetoxy-6,6-dimethyl-3,20-dioxo-19-nor-pregna-4-ene.

19. A pharmaceutical composition containing (i) a therapeutically effective amount of the compound according to claim 18 and (ii) a suitable excipient.

20. The pharmaceutical composition according to claim 19, which is a contraceptive composition, further containing a therapeutically effective amount of a sex steroid.

21. A compound of the formula (I):

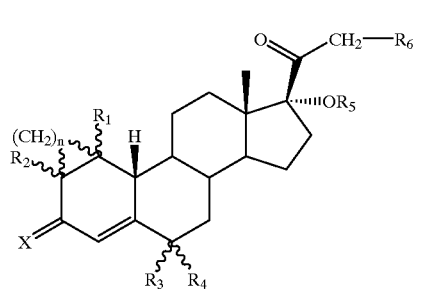

(I)

wherein:
$R_1$, $R_2$ and $R_6$ are hydrogen,
$R_3$, $R_4$ each independently represent hydrogen or a $(C_1-C_6)$alkyl, provided that $R_3$ and $R_4$ are not simultaneously hydrogen,
$R_5$ is a —$COR_7$ group where $R_7$ is methyl,
n is one, and
X is oxygen or a hydroxyimino group.

22. A compound according to claim 21, wherein $R_1$, $R_2$ and $R_4$ are hydrogen, and $R_3$ is a $(C_1-C_6)$alkyl.

23. A compound according to claim 21, which is 17α-acetoxy-1α, 2α-methylene-6α-methyl-3,20-dioxo-19-nor-pregna-4-ene.

24. A pharmaceutical composition containing (i) a therapeutically effective amount of a compound according to claim 21 and (ii) a suitable excipient.

25. The pharmaceutical composition according to claim 24, which is a contraceptive composition, further containing a therapeutically effective amount of a sex steroid.

26. A pharmaceutical composition containing (i) a therapeutically effective amount of a compound according to claim 22 and (ii) a suitable excipient.

27. A pharmaceutical composition according to claim 26, which is a contraceptive composition, further containing a therapeutically effective amount of a sex steroid.

28. A pharmaceutical composition containing (i) a therapeutically effective amount of a compound according to claim 23 and (ii) a suitable excipient.

29. A pharmaceutical composition according to claim 28, which is a contraceptive composition, further containing a therapeutically effective amount of a sex steroid.

30. The compound according to claim 21, which is 17α-acetoxy-1,2α-methylene-6,6-dimethyl-3,20-dioxo-19-nor-pregna-4-ene.

31. A pharmaceutical composition containing (i) a therapeutically effective amount of the compound according to claim 30 and (ii) a suitable excipient.

32. The pharmaceutical composition according to claim 31, which is a contraceptive composition, further containing a therapeutically effective amount of a sex steroid.

* * * * *